United States Patent [19]

Natwick et al.

[11] Patent Number: 5,357,827
[45] Date of Patent: Oct. 25, 1994

[54] TORQUE COMPENSATED CAM ASSEMBLY AND METHOD

[75] Inventors: Vernon R. Natwick, Los Altos; Michael W. Lawless, Boulder Creek, both of Calif.

[73] Assignee: Abbott Laboratories, Abbott Park, Ill.

[21] Appl. No.: 738,585

[22] Filed: Jul. 31, 1991

Related U.S. Application Data

[63] Continuation-in-part of Ser. No. 494,210, Mar. 15, 1990, Pat. No. 5,055,001.

[51] Int. Cl.[5] ............................................. F16H 53/06
[52] U.S. Cl. ......................................... 74/569; 74/54; 74/567
[58] Field of Search ................ 74/57, 55, 56, 54, 567, 74/568 FS, 569

[56] References Cited

U.S. PATENT DOCUMENTS

| | | | |
|---|---|---|---|
| 2,412,397 | 12/1946 | Harper | 103/148 |
| 3,110,194 | 11/1963 | Roman | 74/54 X |
| 3,149,495 | 9/1964 | Riley et al. | 74/54 X |
| 3,543,589 | 12/1970 | Loughran | 74/54 X |
| 3,609,069 | 9/1971 | Martinelli | 417/474 |
| 4,277,226 | 7/1981 | Archibald | 417/38 |
| 4,302,164 | 11/1981 | Manella | 417/474 |
| 4,391,600 | 7/1983 | Archibald | 604/153 |
| 4,406,173 | 9/1983 | Lagain | 74/567 X |
| 4,479,797 | 10/1984 | Kobayashi et al. | 604/153 |
| 4,559,038 | 12/1985 | Berg et al. | 604/153 |
| 4,650,469 | 3/1987 | Berg et al. | 604/131 |
| 4,653,987 | 3/1987 | Tsuji et al. | 417/360 |
| 4,660,482 | 4/1987 | Skogward | 74/54 X |
| 4,690,673 | 9/1987 | Bloomquist | 604/67 |
| 4,728,265 | 3/1988 | Cannon | 417/363 |
| 4,889,613 | 12/1989 | McNeal et al. | 74/54 X |
| 5,055,001 | 10/1991 | Natwick et al. | 417/63 |
| 5,059,393 | 10/1991 | Quenin et al. | 74/54 X |

FOREIGN PATENT DOCUMENTS 2097506  11/1982  United Kingdom .................... 74/54

OTHER PUBLICATIONS

Physics Parts I & II, Halliday Resnick, pp. 261 and 275, John Wiley & Sons, Inc. Publisher (1967).

*Primary Examiner*—Vinh T. Luong
*Attorney, Agent, or Firm*—Christensen, O'Connor, Johnson & Kindness

[57] ABSTRACT

A cam assembly and method for providing a substantially constant load to a motor that drives the cam assembly. A torque compensated cam assembly (142,300) includes a plurality of tracks (140,150,152/310,312,314) that are profiled with a surface that varies radially as the cam rotates, thereby actuating cam followers, each of which rolls along a different track. A tangential force developed by the cam followers as they move over rapid radial changes in the surfaces of the tracks produces a total net torque that at times tends to aid the rotation of the cam and at times tends to impede its rotation. The cam is used in a volumetric pump (30) that accurately delivers a desired volume of fluid at a desire rate. To assist in maintaining the accuracy of these parameters, the torque compensated cam assembly presents a substantially constant load to a motor (146,304) that drives the cam. In one embodiment, the cam assembly includes a torque compensation track (170/316) disposed at one end of the cam, and in another embodiment, the torque compensation track is disposed circumferentially around the cam. A torque compensation roller (172,320) is biased against the torque compensation track by a flexure (174), providing a force that develops the required compensating torque. The profile of the torque compensation track is defined so as to produce a torque that is substantially equal in magnitude, but opposite in the direction, that it tends to rotate the cam assembly, compared to the net torque developed by the cam followers.

20 Claims, 9 Drawing Sheets

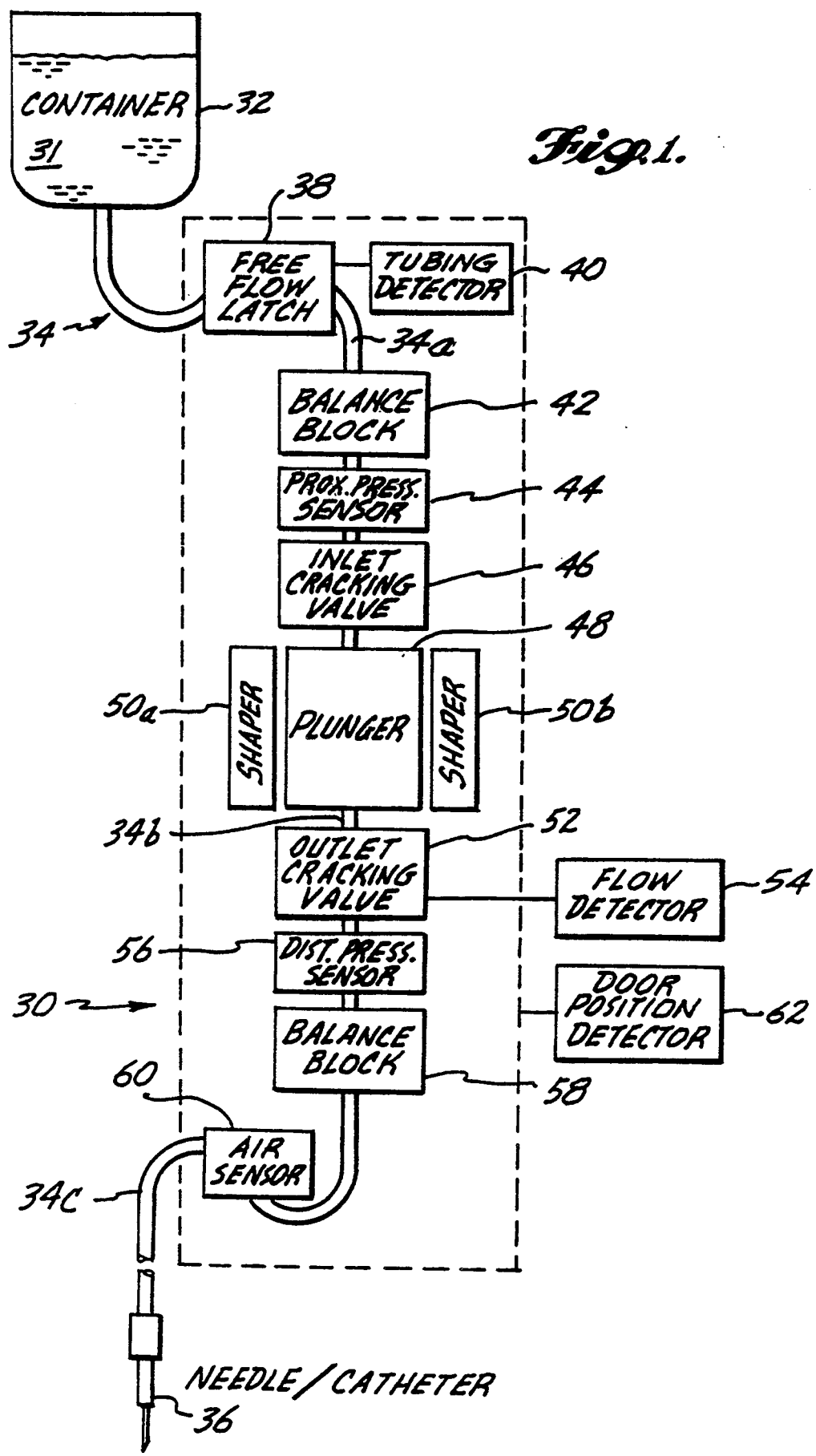

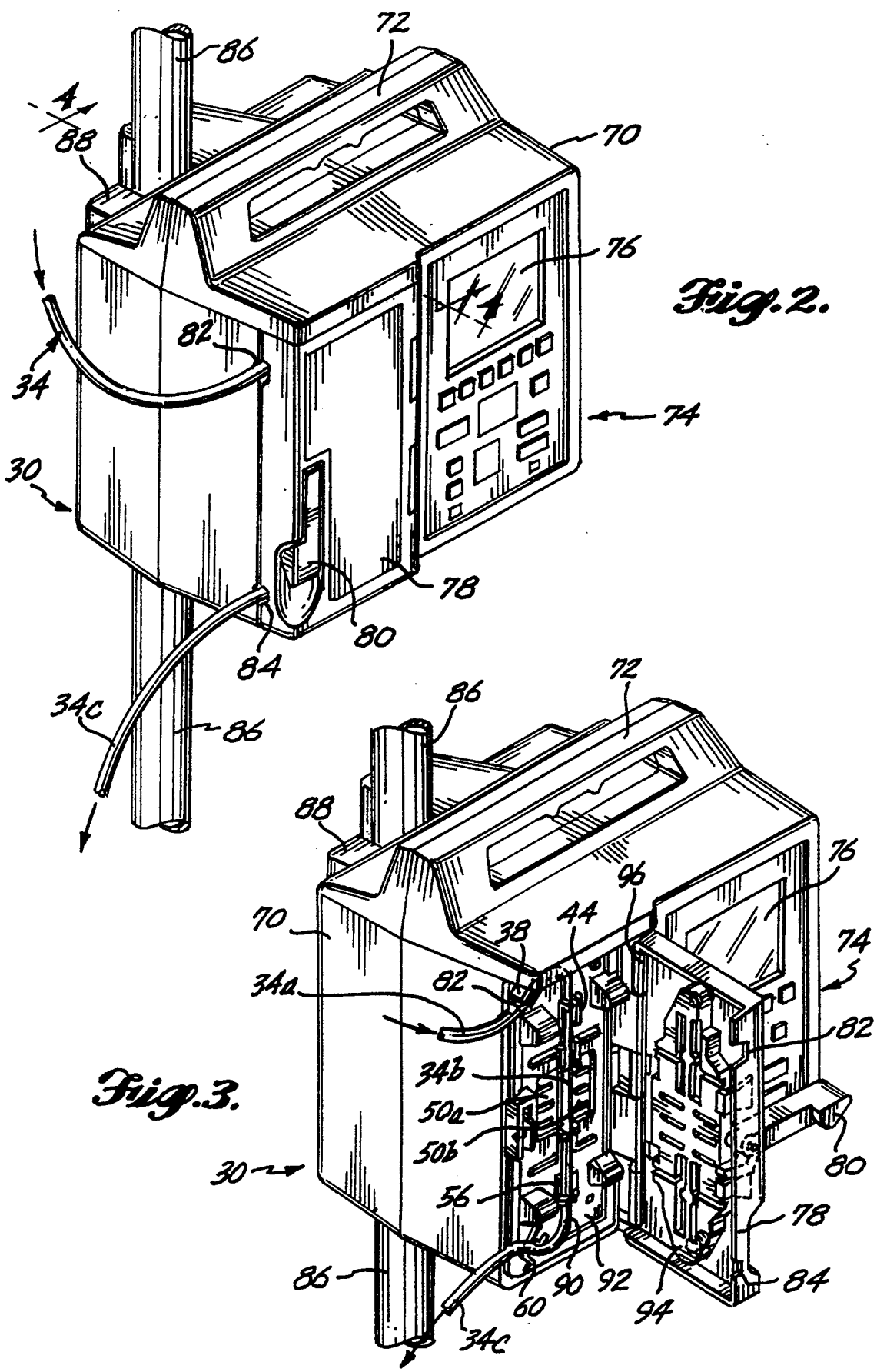

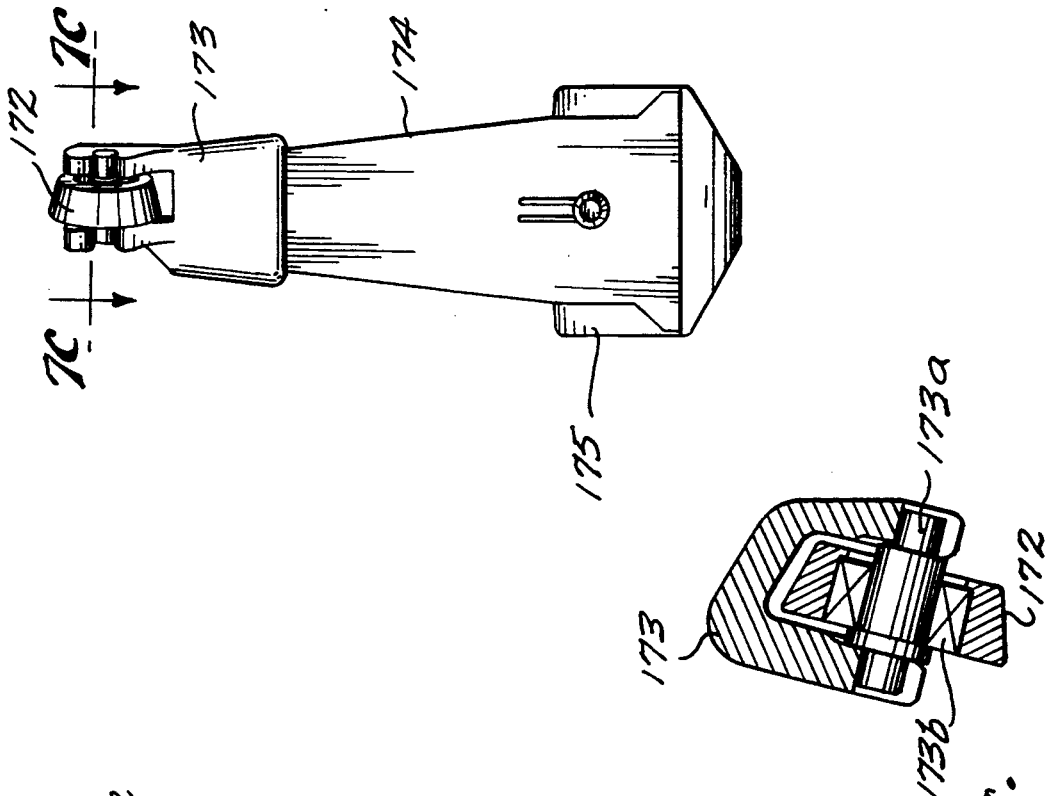
Fig. 7B.
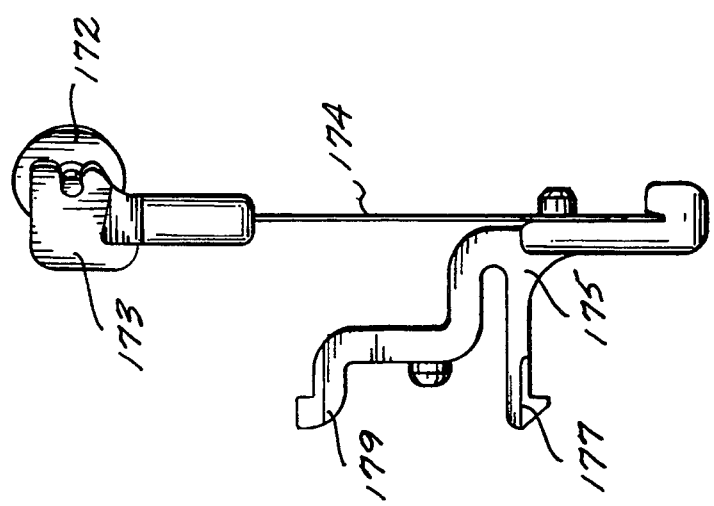
Fig. 7A.
Fig. 7C.

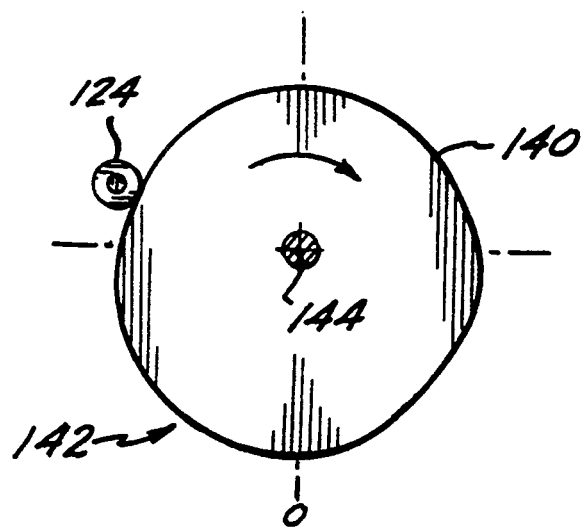
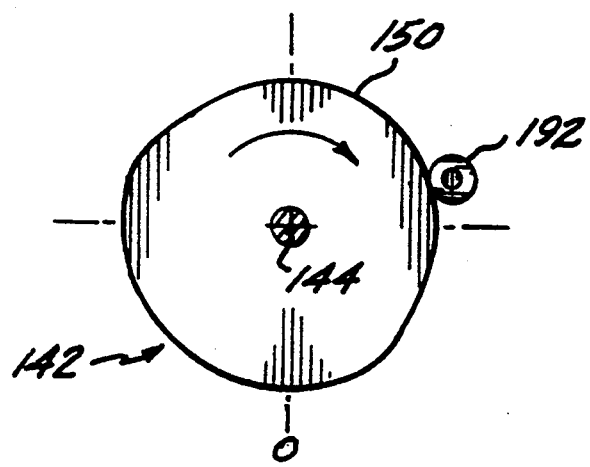
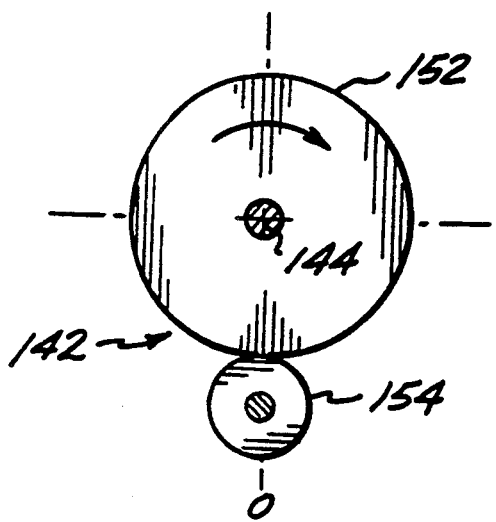

TORQUE COMPENSATED CAM ASSEMBLY AND METHOD

RELATED APPLICATIONS

This document is a continuation-in-part of prior U.S. patent application Ser. No. 494,210, filed on Mar. 15, 1990 now U.S. Pat. No. 5,055,001. The benefit of the filing date of the prior application is hereby claimed under 35 U.S.C. § 120.

TECHNICAL FIELD

This invention generally pertains to a cam assembly that actuates one or more cam followers in a reciprocating pump or other device, and specifically, to a rotatably driven cam in such an assembly that is subject to a torque developed as one or more cam followers ride over the cam, particularly in a cam assembly used in a peristaltic pump.

BACKGROUND OF THE INVENTION

A peristaltic pump displaces liquid by repetitively compressing a section of the flexible tube comprising an IV line. This line is threaded through a channel formed in the pump and extends unbroken, from a drug container to a patient. One type of peristaltic pump has a linear channel in which the IV line is threaded and is thus referred to as a linear (or traveling wave) peristaltic pump. The linear peristaltic pump includes a plurality of finger-like plungers that are sequentially actuated by cams mounted along a motor driven shaft. Liquid within the section of tubing that extends along the linear channel is advanced along the tubing's longitudinal axis by the advancing wave-like compression of the fingers. An example of such a pump is disclosed in U.S. Pat. No. 4,479,797.

Inlet and outlet valves and a single liquid displacement plunger are used in another type of peristaltic pump. Each pumping cycle in this type of pump begins with the outlet valve closed and the inlet valve open. Fluid flows from the source container into a short section of tubing that is disposed between the inlet and outlet valve. After this section of tubing has filled with liquid, the inlet valve closes and the outlet valve opens. The plunger then compresses the short section of tubing between the valves, displacing the liquid contained therein, and forcing it from the pump. U.S. Pat. No. 4,559,038 discloses a peristaltic pump of this type.

The rate at which fluid is delivered by each type of positive displacement pump discussed above is normally controlled by the rate at which the pump operates, e.g., the rotational rate of the rotating arm in that type of peristaltic pump. Furthermore, the accuracy with which a given rate or volume of fluid flow can be achieved by these pumps is dependent upon the pressure of the fluid at the input of the pump and the back pressure at its output. Since the flexible tubing in a peristaltic pump defines a compliant pumping chamber, the volume of fluid that fills the pumping chamber is affected by the head pressure of the fluid from the drug container. Similarly, the volume of fluid delivered at the output of the pump depends on the back pressure of the fluid downstream of the outlet. The single plunger type of peristaltic pump has positive closure inlet and outlet valves and is particularly sensitive to head and back pressures because the volume of the pumping chamber disposed between the valves and the amount of fluid that fills the chamber generally must be constant to provide an accurate and consistent rate of flow from the pump. A superior single plunger peristaltic pump that is capable of supplying fluid at a desired flow rate and pressure, generally independent of head pressure and back pressure downstream of the pump is disclosed in the above referenced commonly assigned U.S. patent application Ser. No. 494,210, filed Mar. 15, 1990.

In the single plunger type of peristaltic pump, the plunger should compress the tubing uniformly and consistently with each pumping stroke to provide an accurate and consistent rate of fluid flow from the pump. Since the plunger is typically driven by a rotating cam, it is essential that the cam rotate smoothly at a constant speed. The plunger and valves in the peristaltic pump are actuated by cam followers that ride along radially varying profiles defining different circumferential tracks on the cam. As the cam followers roll along the tracks, the slope of each track's profile causes a tangential force to be developed that produces a rotational torque tending either to aid or to impede the rotation of the cam. The net torque thus developed from the forces exerted by all of the cam followers can cause the rotational speed of the cam to increase or decrease at various points in its rotation, due to changes in the load presented to a motor that rotatably drives the cam. Such rotational speed changes affect the accuracy with which the pump delivers fluid, assuming that servo-speed control is not provided, and adversely impacts audible noise and power consumption.

In consideration of these problems that exist with the cam assemblies in prior art peristaltic pumps and other devices using cam drives, it is an object of the present invention to provide a torque compensated cam assembly that maintains a substantially constant load on a prime mover used to rotate a cam in the cam assembly. Another object of this invention is to provide a cam assembly in which the cam rotates at a rate substantially independently of loading developed due to interaction between one or more cam followers and tracks formed on the cam. Yet a further object is to provide a cam assembly that can be used in a positive displacement fluid pump to deliver fluid to an output port of the pump at a predefined pressure. These and other objects and advantages of the present invention will be apparent from the attached drawings and the Description of the Preferred Embodiments that follows.

SUMMARY OF THE INVENTION

In accordance with the claimed invention, a torque compensated cam assembly is provided that is particularly useful in a reciprocating pump to maintain a substantially constant load on a prime mover that drives the pump. The cam assembly includes a cam rotatably driven by the prime mover to rotate about an axis. Cam follower means contact the cam at a varying radial distance from the axis as the prime mover rotates the cam about its axis, producing a torque that varies with a rotational position of the cam. At times, the torque is directed so as to aid the rotation of the cam, and at times, is directed so as to impede its rotation by the prime mover. Torque compensation means are included for producing a torque that is generally equal in magnitude, but opposite in the direction that it tends to rotate the cam, compared to the torque produced by the cam follower means. As a result, a generally constant load is presented to the prime mover as it rotatably drives the cam.

The torque follower means preferably comprise a plurality of cam followers, each of which follow a different path disposed circumferentially about the cam, as the prime mover drivingly rotates the cam. Each path comprises a surface that is at a varying radial distance about the axis of the cam.

The torque compensated means comprise a spring-biased roller that rolls along a track disposed on the cam. This track has a predefined profile so as to provide the compensating torque. In one form of the invention, the track is disposed on one end of the cam, around the axis of the cam, and is generally circular in shape. The predefined profile of the track varies in a direction generally parallel to the axis of the cam. The roller is preferably tapered at a predefined angle between a larger diameter side and a smaller diameter side. This predefined angle compensates for differences in linear velocity of radially spaced-apart points on the track. By mounting the roller on an elastic flexure, a spring-biasing force is provided sufficient to produce the compensating torque as the roller moves along the track.

Alternatively, the torque compensation means can comprise a spring-biased roller that rolls along a track formed circumferentially about the cam and having a predefined radially varying profile selected to provide the compensating torque. The cam follower means also comprise a spring-biased roller that rolls circumferentially around the cam, along a path that is disposed at a varying radial displacement from the axis of the cam, as a function of angular position about said axis.

A method for maintaining a generally constant load on a prime mover that rotatably drives a cam is another aspect of this invention. The method includes steps that are generally consistent with the functions provided by the elements comprising the cam assembly.

BRIEF DESCRIPTION OF THE DRAWINGS

FIG. 1 is a schematic block diagram of a volumetric pump in which the present invention is used;

FIG. 2 is an isometric view of the volumetric pump, showing an access door that is closed and latched in place, securing a flexible tube within the pump;

FIG. 3 is an isometric view, similar to that shown in FIG. 2, but with the access door shown in an open position, so as to disclose the path followed by the flexible tube through the volumetric pump;

FIGS. 7A, 7B, and 7C are respectively a side view and a front view of the cam follower assembly, and a cross-sectional view of a torque compensation roller and a mounting head therefor, as used in the first embodiment of the present invention;

FIG. 8 illustrates a profile of the inlet cracking valve cam track;

FIG. 9 illustrates a profile of the outlet cracking valve cam track;

FIG. 10 illustrates a profile of the plunger cam track;

DESCRIPTION OF THE PREFERRED EMBODIMENTS

Volumetric Pump

Figure 4:
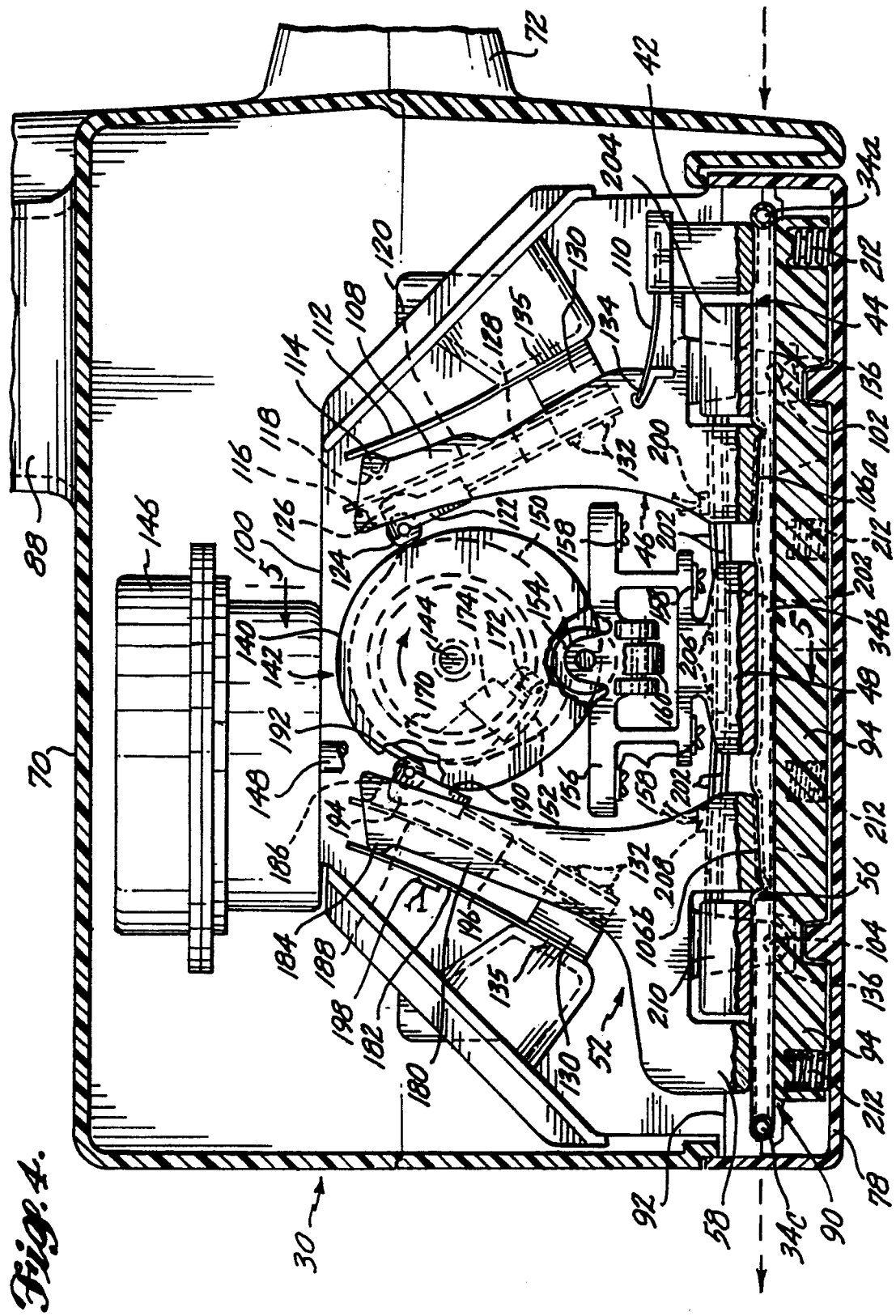
FIG. 4 is a longitudinal cross section of the pump assembly shown in FIGS. 2 and 3, illustrating the disposition of a first embodiment of the present invention using hidden lines.

The term "volumetric pump" is applied to a pump in which the present invention is used, because the term appropriately emphasizes one of the pump's more important advantages that the present invention helps to achieve. Specifically, during each pumping stroke, the volumetric pump consistently and repeatedly displaces a defined volume of fluid at a defined pressure, thereby ensuring that a desired rate of fluid flow is accurately delivered by the pump. By providing consistency in the force required to drive the pump throughout the pumping cycle, the present invention helps to insure that the desired flow rate is accurately produced.

In FIG. 1, a volumetric pump that includes the present invention is generally illustrated in a block diagram at reference numeral 30. Volumetric pump 30 comprises a number of components that are serially arranged along a fluid path through the pump. A liquid 31 that is administered by volumetric pump 30 is supplied from a container 32 through flexible tubing 34. Liquid 31 enters volumetric pump 30 through a proximal portion 34a of the flexible tubing. The fluid path continues through a pumping portion 34b and exits the pump through a distal portion 34c of the flexible tubing. Distal portion 34c of the flexible tubing is connected to a needle/catheter 36 that is used to introduce liquid 31 flowing from the pump intravenously into a patient. Of course, volumetric pump 30 may also be used in other applications wherein distal portion 34c of the flexible tubing is connected to some other apparatus disposed downstream of volumetric pump 30.

Flexible tubing 34 is continuous, but for purposes of this disclosure, is referred to as divided into the proximal, pumping, and distal portions 34a, 34b, and 34c, respectively; preferably, it comprises a polyvinyl chloride (PVC) disposable tube set, such as is customarily used to administer fluids intravenously to a patient. The tubing may have a 0.137" O.D. and 0.100" I.D.

In this application of the volumetric pump, it is desirable to prevent free flow of liquid 31 from container 32 into the patient. For this reason, volumetric pump 30 includes a free flow latch 38, which clamps proximal portion 34a of the flexible tubing to prevent liquid 31 from container 32 flowing freely into a patient, due to head pressure. Free flow latch 38 does not restrict fluid flow during the normal pumping operation of volumetric pump 30, but is configured to automatically clamp proximal portion 34a of the flexible tubing when a door 78 (shown in FIGS. 2 and 3) on volumetric pump 30 is opened. While door 78 is closed, free fluid flow through volumetric pump 30 is otherwise precluded by volumetric pump 30, as explained below. The position of door 78 is sensed by a door position detector 62, producing a signal that prevents operation of volumetric pump 30 when door 78 is open. Similarly, a tubing detector 40 is interconnected to free flow latch 38, and produces a signal indicative of the presence of flexible tubing 34 within free flow latch 38; operation of volumetric pump 30 is inhibited if the signal indicates that the flexible tubing is not in place.

A balance block 42 rests against proximal portion 34a of flexible tubing 34 and serves to compensate for variations or changes in the elasticity of flexible tubing 34. The function and operation of balance block 42 are more fully explained below.

Next in the serial arrangement of components along the fluid path within volumetric pump 30 is a proximal pressure sensor 44, which operates to sense the pressure of fluid within proximal portion 34a of the flexible tubing. Proximal pressure sensor 44 produces a signal indicative of fluid pressure in this portion of flexible tubing 34 for use in monitoring the operation of the pump and to determine if proximal portion 34a has become occluded.

A key element in the operation of volumetric pump 30 is an inlet cracking valve 46, disposed immediately downstream of proximal pressure sensor 44. Inlet cracking valve 46 functions in cooperation with a plunger 48 and an outlet cracking valve 52, which are disposed sequentially downstream of the inlet cracking valve, to provide the displacement of a volumetric quantity of fluid from pumping portion 34b of the flexible tubing by volumetric pump 30 and to generally isolate the volumetric pump from variations in proximal and distal fluid pressure, due, for example, to variations in the elevation of container 32, or variations in the back pressure of fluid in distal portion 34c of the flexible tubing. A flow detector 54 is interconnected with outlet cracking valve 52 and produces a signal indicating whether fluid is successfully being pumped by volumetric pump 30 into distal portion 34c. Tubing shapers 50a and 50b are disposed at each side of plunger 48 and act to rapidly reform pumping portion 34b of the flexible tubing as it refills with fluid during each pump cycle, insuring consistent volumetric refill with each pumping stroke.

A distal pressure sensor 56 produces a signal indicative of the fluid pressure within distal portion 34c of the flexible tubing, i.e., the output pressure of volumetric pump 30. The distal fluid pressure is used for monitoring the operation of volumetric pump 30 and for sensing an occlusion of flexible tubing 34.

Immediately adjacent distal pressure sensor 56 is a balance block 58. Cooperating with outlet cracking valve 52, balance block 58 compensates for changes or variations in the stiffness or elasticity of flexible tubing 34, in a manner similar to that in which balance block 42 cooperates with inlet cracking valve 46.

An air sensor 60 is the last component along the fluid path through volumetric pump 30. Air sensor 60 detects the presence of air bubbles larger than a predefined volume in the fluid discharged from the volumetric pump, and produces a signal indicative of such air bubbles, which stops volumetric pump 30 and initiates an alarm to prevent a potentially harmful air embolism forming in the fluid being introduced into a patient through needle/catheter 36. Air sensor 60 comprises a generally conventional piezoelectric ultrasonic transmitter and receiver (not separately shown), spaced apart on opposite sides of distal portion 34c of the flexible tubing. The transmitter produces an ultrasonic signal that is transmitted through flexible tubing 34 to the receiver. Liquid present in flexible tubing 34 between the transmitter and receiver conveys the ultrasonic signal much more efficiently than does an air bubble. The receiver produces an electronic signal in response to the level of the ultrasonic signal reaching it, the amplitude of the electronic signal indicating whether an air bubble or liquid is present in flexible tubing 34 between the transmitter and receiver. Details of air sensor 60 are not illustrated because such devices are generally well known to those of ordinary skill in this art.

In FIGS. 2 and 3, volumetric pump 30 is illustrated in isometric view. As shown therein, volumetric pump 30 includes a molded plastic housing 70, having a handle 72 on its upper surface to facilitate carrying the volumetric pump to a point of use. A control panel 74 and a display 76 are disposed on the right side of the front surface of volumetric pump 30, and are respectively used by an operator for entry and display of data that controls the volumetric pump.

On the back of housing 70 is formed a clamp 88, which is used to removably attach volumetric pump 30 to a post 86, for example at the bedside of a patient. Details of clamp 88 are not shown since it is generally typical of those used with other types of medical apparatus intended for connection to vertical posts.

In FIG. 2, door 78 is shown latched closed, the appropriate disposition for use of the volumetric pump, while in FIG. 3, door 78 is shown in an open position. A latch handle 80 is pivoted upwardly so that door 78 can be swung open on a hinge 96, giving access to an inner cover 92 that defines the path followed by flexible tubing 34 through volumetric pump 30. As noted above, when door 78 is opened while flexible tubing 34 is threaded through the volumetric pump and connected to container 32, free flow latch 38 clamps the flexible tubing closed to prevent liquid 31 in container 32 from free flowing through flexible tubing 34. The mechanism that actuates free flow latch 38 when door 78 is opened is not shown since it is not particularly relevant to the present invention.

Flexible tubing 34 is angled upwardly where it passes through an entry slot 82 formed on the side of door 78, insuring that any of liquid 31 leaking from container 32 drips from a loop formed in flexible tubing 34 and does not run into volumetric pump 30. After door 78 is swung open, flexible tubing 34 is readily threaded into a channel 90 defined along the longitudinal center of inner cover 92. An exit slot 84, formed in the lower side portion of door 78, overlies distal portion 34c of the flexible tubing. A pressure plate 94 disposed on the inner surface of door 78 comes into contact with flexible tubing 34 along the length of channel 90 as door 78 is closed and latched with handle 80.

Figure 5:
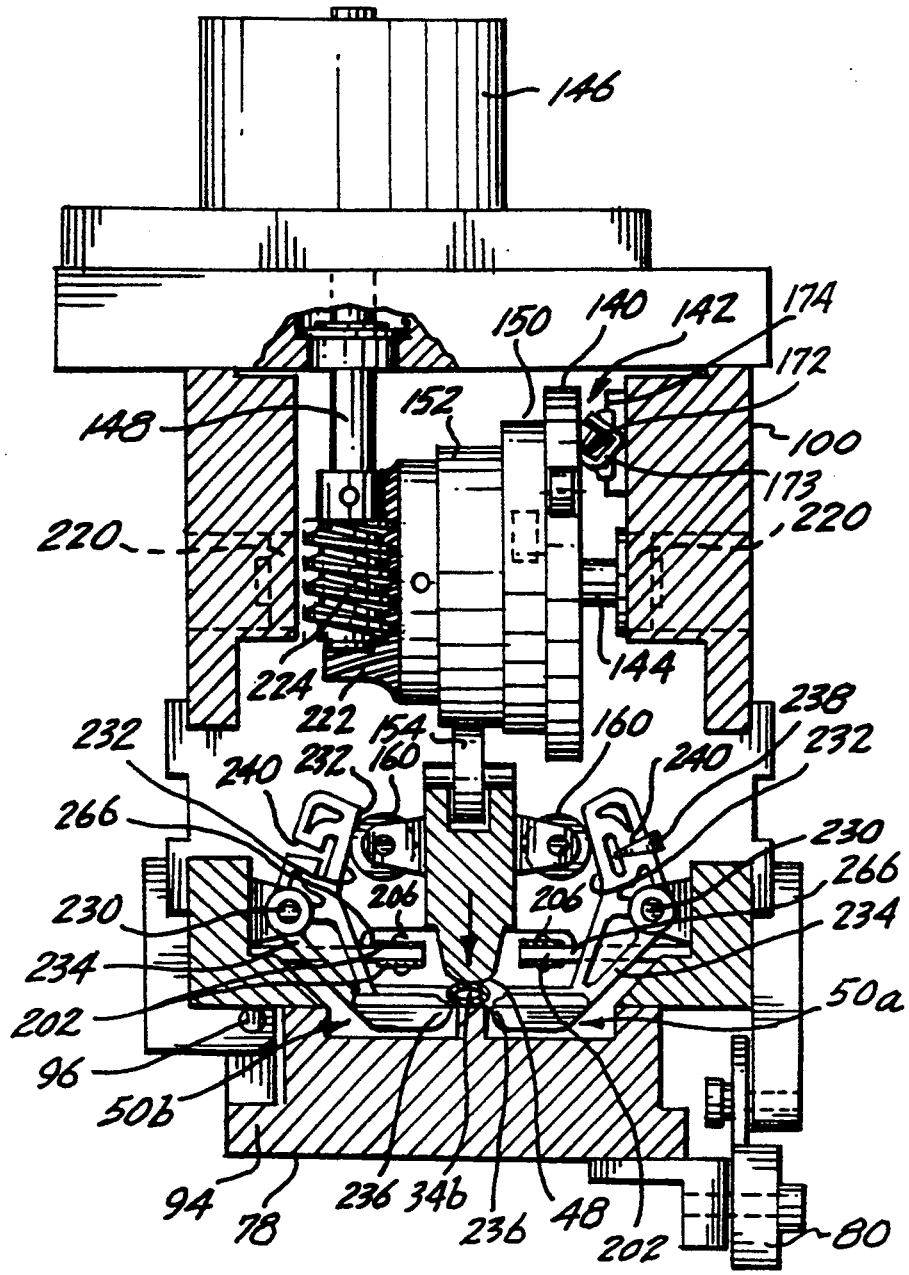
FIG. 5 is a schematic transverse cross section of the volumetric pump, illustrating the first embodiment of the present invention.
Figure 6:
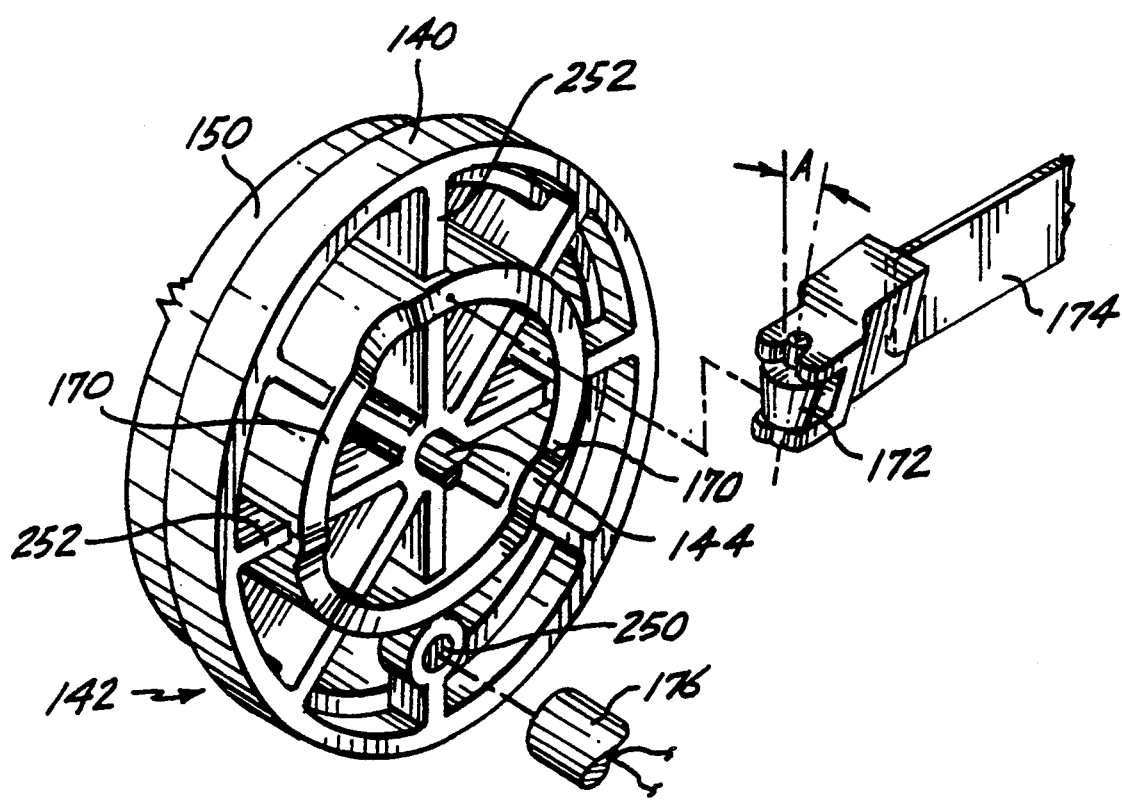
FIG. 6 is an isometric view of one end of a portion of the cam assembly on which a torque compensation track is disposed and a portion of a torque compensation follower, in accordance with the first embodiment of the present invention.

FIGS. 4, 5, and 6 show details of the interior of volumetric pump 30. Pressure plate 94 defines a reference plane or surface in respect to each of the components of volumetric pump 30 that act to compress flexible tubing 34 and is mounted so that it floats on a plurality of helical coiled springs 212. Springs 212 bias pressure plate 94 away from the inner surface of door 78. When door 78 is closed, pressure plate 94 contacts inner cover 92 at several points. Helical springs 212, which are relatively stiff, are thus slightly compressed, and therefore accommodate variations in the tolerances of door 78 and other related parts that arise during construction of volumetric pump 30. Such tolerances might otherwise affect the position of the reference plane defined by pressure plate 94.

Most of the components comprising volumetric pump 30 are mounted on a frame 100 within housing 70. For example, frame 100 includes inlet cracking valve pivot mounts 102 and outlet cracking valve pivot mounts 104, about which inlet cracking valve 46 and outlet cracking valve 52 respectively pivot.

Inlet cracking valve 46 contacts proximal portion 34a of the flexible tubing along a valve face 106a. Similarly, outlet cracking valve 52 contacts distal portion 34c of the flexible tubing along a valve face 106b. The pivotal motion of inlet cracking valve 46 and outlet cracking valve 52 respectively varies the force with which valve faces 106a and 106b contact flexible tubing 34 to control fluid flow therethrough by compressing the flexible tubing against pressure plate 94. Plunger 48 compresses pumping portion 34b of the flexible tubing against pressure plate 94 to displace fluid from within a pumping chamber defined between the inlet and outlet cracking valves 46 and 52. In part because volumetric pump 30 includes inlet and outlet cracking valves 46 and 52, it operates differently than the prior art plunger type peristaltic pumps, as will be apparent from the following disclosure.

An inlet valve arm 108 extends upwardly from valve face 106a on inlet cracking valve 46. Disposed generally above inlet cracking valve pivot mounts 102 are flat metal spring flexures 110, which connect balance block 42 to a slot 134, formed on the back side of inlet valve arm 108. Flexures 110 are snapped within slot 134 and flex to enable inlet valve arm 108 to pivot valve face 106a away from pressure plate 94 through a greater angle that would otherwise be possible, without closing off fluid flow through flexible tubing 34 due to compression of the flexible tubing by balance block 42. Inlet cracking valve pivot mounts 102 are connected to downwardly depending pivot arms 136 on inlet cracking valve 46, at each side of flexible tubing 34, and are centered between balance block 42 and valve face 106a. The stiffness of flexible tubing 34 acts on balance block 42 and flexures 110, and the balance force developed as a function of this stiffness (or lack of elasticity) tends to pivot inlet valve face 106a against pressure plate 94, thereby increasing the force exerted by that part of inlet cracking valve 46 to compress the flexible tubing. The stiffness of flexible tubing 34 also resists compression by inlet valve face 106a to a similar extent. Accordingly, variations in the elasticity of flexible tubing 34 that affect the force required for inlet valve face 106a to compress the tubing are automatically compensated for by balance block 42.

Inlet cracking valve 46 operates in three distinct modes, the force applied by valve face 106a to compress flexible tubing 34 being substantially different in each mode. Two different spring-bias forces act on inlet valve arm 108. A fluid flow control force is applied to inlet valve arm 108 by a flat metal spring cracking flexure 112, acting against a knob 114, which is disposed at one end of inlet valve arm 108. The additional force necessary to compress flexible tubing 34 sufficiently to completely close off fluid flow past inlet cracking valve 46 is supplied by a flat metal spring closure flexure 120. Closure flexure 120 acts upon a side arm 116, disposed on one side of inlet valve arm 108. The combined force provided by cracking flexure 112 and closure flexure 120 (in addition to the balance force provided by balance block 42) pivots inlet cracking valve 46 about a pivot axis extending through inlet cracking valve pivot mounts 102, to completely block fluid flow through flexible tubing 34.

An inlet valve cam follower 122 selectively determines whether cracking flexure 112 and closure flexure 120 apply force against inlet valve arm 108 and thus determines the three modes in which inlet cracking valve 42 operates. Inlet valve cam follower 122 includes a roller 124 rotatably mounted in a hood 126, which is attached via an inlet follower flexure 128 to a plurality of blocks 130. Blocks 130 are also used in mounting cracking flexure 112 and closure flexure 120 to a bracket 135 and to provide appropriate spacing between these flexures and bracket 135. Bolts 132 connect the ends of each of these flexures to bracket 135, which comprises a portion of frame 100.

Roller 124 rolls along an inlet valve cam track 140, disposed on a rotating cam assembly 142. Cam assembly 142 turns on a camshaft 144, which at each of its ends is mounted to frame 100 in bearings 220 (see FIG. 5). A motor shaft 148 extends downwardly from a motor 146, and a helical gear 224 on motor shaft 148 drivingly engages gear teeth 222, which are formed on one end of cam assembly 142, causing the cam assembly to rotate in a clockwise direction, as viewed in FIG. 4. The radial distance between camshaft 144 and the point where roller 124 contacts the surface of inlet valve cam track 140 varies as cam assembly 142 rotates, moving inlet valve cam follower 122 radially back and forth so as to control the forces applied to inlet valve arm 108. Specifically, as hood 126 is forced radially back against closure flexure 120, it lifts the closure flexure away from side arm 116, eliminating the force normally exerted by the closure flexure against the side arm and thereby reducing the total force exerted by valve face 106a against flexible tubing 34. In this configuration, inlet cracking valve 46 is in a "cracking mode."

As hood 126 moves further radially outward, closure flexure 120 contacts a "V-shaped" side arm 118 that is formed on the side of inlet valve arm 108, causing inlet valve arm 108 to pivot valve face 106a away from pressure plate 94. In this configuration, inlet cracking valve 46 is in an open mode, wherein liquid 31 freely flows from container 32 through proximal portion 34a of the flexible tubing and into pumping portion 34b. Flexures 110 bend as valve face 106a pivots away from pressure plate 94, so that balance block 42 does not close off fluid flow through proximal portion 34a of the flexible tubing.

When both closure flexure 120 and cracking flexure 112 are allowed to act on inlet valve arm 108, valve face 106a compresses flexible tubing 34 against pressure plate 94 sufficiently to completely block fluid flow through the flexible tubing. In this configuration, inlet cracking valve 46 is in a "closed mode."

An outlet valve cam track 150 is disposed between inlet valve cam track 140 and a plunger cam track 152. Plunger cam track 152 provides a surface at varying radii about camshaft 144 for actuating plunger 48 to compress pumping portion 34b of the flexible tubing against pressure plate 94. A roller 154 is rotatably mounted on a base 156 of plunger 48, and is thus disposed to roll along plunger cam track 152. Also mounted on base 156, at opposite sides of roller 154, are tubing shaper rollers 160. The disposition of tubing shaper rollers 160 is more clearly shown in FIG. 5, and their operation in respect to shaping flexible tubing 34 is disclosed in detail below.

As shown using hidden lines in FIG. 4, the back side of cam assembly 142 includes a torque compensation track 170 in accordance with the present invention. A conically-shaped or tapered torque compensation roller 172 rolls along torque compensation track 170, applying a rotational torque to cam assembly 142 that compensates for an opposite torque resulting from rapid changes in the shape of inlet valve cam track 140, outlet valve cam track 150, and plunger cam track 152. Torque compensation roller 172 is mounted on a flat metal spring torque compensation flexure 174 that applies a biasing force to the torque compensation roller, forcing it against torque compensation track 170 on cam assembly 142. Further details of the torque compensation assembly are disclosed below.

Like inlet cracking valve 46, outlet cracking valve 52 has a generally "Y-shaped" configuration and includes an outlet valve arm 180, which is connected to outlet valve face 106b and to balance block 58. On opposite sides of flexible tubing 34, pivot arms 136 extend downwardly, connecting to outlet cracking valve pivot mounts 104 on frame 100. Balance block 58 rests on distal portion 34c of the flexible tubing and develops a force proportional to the stiffness (or lack of elasticity) of flexible tubing 34, which tends to increase the compression force applied against flexible tubing 34 by outlet valve face 106b to compensate or balance the resistance to compression caused by the stiffness (or lack of elasticity) of the flexible tubing. Just as balance block 42 compensates for changes or variations in elasticity of the flexible tubing in respect to inlet cracking valve 46, balance block 58 compensates for such changes and variations in respect to outlet cracking valve 52. However, since outlet cracking valve 52 is never pivoted to an open mode like inlet cracking valve 46, balance block 58 is integrally attached to outlet valve arm 180. Flexures 110 are not required, since the extent of pivotal rotation of outlet cracking valve 52 is substantially more limited than for inlet cracking valve 46. At all times, even when volumetric pump 30 is not pumping fluid, either inlet cracking valve 46 or outlet cracking valve 52 is in its closed mode, preventing liquid 31 from free flowing through flexible tubing 34.

As shown in FIG. 4, outlet cracking valve 52 is in its closed mode, compressing flexible tubing 34 against pressure plate 94 sufficiently to block fluid flow therethrough. In this configuration, a flat metal spring cracking flexure 182 applies force against a knob 184 on the top of outlet valve arm 180. In addition, a flat metal spring closure flexure 188 applies a biasing force against a side arm 186 that extends outwardly from the side of outlet valve arm 180.

An outlet valve cam follower 190 includes a roller 192, which rolls along outlet valve cam track 150. Roller 192 is rotatably mounted within a hood 194, which is connected to a flat metal spring follower flexure 196. Follower flexure 196 spring biases roller 192 into contact with outlet valve cam track 150. The lower ends of follower flexure 196, cracking flexure 182, and closure flexure 188 are all secured at blocks 130 to bracket 135 by bolts 132, just as the corresponding elements are in respect to inlet cracking valve 46. As outlet valve cam follower 190 follows outlet valve cam track 150, hood 194 periodically contacts closure flexure 188, lifting it away from side arm 186 so that the flow control force provided by cracking flexure 182, added to the balance force developed by balance block 58, is transmitted to valve face 106b, thereby compressing flexible tubing 34 against pressure plate 94 with a cracking force. In this configuration, outlet cracking valve 52 is in its cracking mode.

As plunger 48 compresses pumping portion 34b of the flexible tubing against pressure plate 94, the pressure developed by liquid trapped between inlet cracking valve 46, which is closed, and outlet cracking valve 52 acts on valve face 106b, in opposition to the cracking force produced by cracking flexure 182 and balance block 58. As the force developed by the fluid pressure reaches a predetermined level sufficient to cause outlet cracking valve 52 to pivot open slightly, liquid 31 flows past the outlet cracking valve from pumping portion 34b of the flexible tubing. Liquid 31 is thus delivered by volumetric pump 30 at a predefined cracking pressure.

A strain gauge 198 is mounted to cracking flexure 182. Strain gauge 198 develops an output signal corresponding to the stress developed in cracking flexure 182, therefore indicating the pivotal motion of outlet valve arm 180 as it rotates to allow fluid flow past outlet cracking valve 52. Accordingly, strain gauge 198 comprises flow detector 54 for determining whether fluid is being pumped through distal portion 34c of the flexible tubing as a result of displacement by plunger 48. If pumping portion 34b of the flexible tubing contains a relatively large proportion of air or other compressible gaseous fluid, plunger 48 cannot develop sufficient fluid pressure to overcome the cracking force exerted by cracking flexure 182 and balance block 58. As a result, strain gauge 198 fails to detect the pivotal motion of outlet valve arm 180, indicating that fluid flow past outlet cracking valve 52 has not occurred during a pumping stroke of plunger 48. Accordingly, the signal from strain gauge 198 can be used to detect whether container 32 has run dry or whether flow of liquid 31 into volumetric pump 30 has otherwise been interrupted. The signal produced by strain gauge 198 is simply a "go/no-go" signal as opposed to a signal that is accurately proportional to the movement of outlet valve arm 180. This go/no-go signal is used to stop volumetric pump 30 and initiate an alarm when the expected fluid flow is not obtained, thereby alerting medical personnel of the problem so that it can be corrected.

Instead of strain gauge 198, various other types of motion sensors may be used to produce a signal indicative of the pivotal motion of outlet valve arm 180. For example, outlet valve arm 180 can be connected to a linear variable displacement transformer (LVDT) that uses motion to produce a signal corresponding to a relative change in the magnetic coupling between two electro-magnetic coils, or may comprise a variable capacitor that changes capacitance value as outlet valve arm 180 pivots. Similarly, a Hall sensor or optical sensor can be used to detect pivotal motion of outlet valve arm 180, and thus may serve as alternative types of flow detectors.

Proximal pressure sensor 44 comprises a block 204, which is spring biased into contact with proximal portion 34a of the flexible tubing, and is disposed between inlet cracking valve 46 and balance block 42. A spring-bias force for proximal pressure sensor 44 is provided by two pairs of longitudinally-extending flexures 202, disposed on each side of plunger 48. Flexures 202 are connected to support plates 266 on frame 100 by fasteners 206 at about the midpoint of the flexures. One of the four flexures 202 connecting block 204 to support plates 266 includes a strain gauge 200, which responds to stress developed in that flexure 202 as a function of fluid pressure within proximal portion 34a of the flexible tubing. As the fluid pressure increases within this portion of flexible tubing 34, flexures 202 connected to block 204 experience increased stress, producing a corresponding change in the output signal from strain gauge 200.

Similarly, distal pressure sensor 56 comprises a block 210, which is connected to the other ends of flexures 202. A strain gauge 208 is disposed on one of the four flexures, intermediate block 210 and one of the support plates 266. Strain gauge 208 produces a signal corresponding to the fluid pressure within distal portion 34c of the flexible tubing, based upon stress developed in flexures 202 as a result of that pressure. Distal pressure sensor 56 can be used to determine if distal portion 34c of the flexible tubing has been kinked, interrupting fluid flow through flexible tubing 34, for example, as might occur if a patient rolled over onto flexible tubing 34. Such a condition causes a notable increase in the distal fluid pressure that triggers an alarm and shuts off volumetric pump 30.

In FIG. 5, details of tubing shapers 50a and 50b are disclosed. Since it is preferable to use relatively low cost PVC tubing in connection with volumetric pump 30, tubing shapers 50a and 50b are provided to ensure consistent operation and volumetric capacity of pumping portion 34b of the flexible tubing throughout the entire operating range of volumetric pump 30. At relatively high pumping rates, PVC tubing does not fully recover to its normal, round, uncompressed shape from a compressed condition rapidly enough to fill completely with fluid. Accordingly, the volumetric displacement of fluid within the PVC tubing that occurs with each pumping stroke is less than desired. To avoid this problem, tubing shapers 50a and 50b force pumping portion 34b of the flexible tubing to recover rapidly to its maximum volumetric capacity, i.e., to open sufficiently so that the desired amount of liquid 31 fills the pumping chamber defined by pumping portion 34b of the flexible tubing.

Each tubing shaper 50a and 50b comprises an angled arm 234, terminating at one end in a longitudinally-extending jaw 236. Arms 234 are attached to frame 100 at pivot mounts 230, about which arms 234 rotate as tubing shaper rollers 160 roll along inner surfaces 232 of arms 234. Thus, the reciprocating up-and-down motion of plunger 48 along its reciprocation axis inherently acts on tubing shaper rollers 160 in "lock-step", causing jaws 236 to pinch pumping portion 34b of the flexible tubing at the proper time, thereby reforming flexible tubing 34 into the required pumping volume or capacity as plunger 48 lifts away from pressure plate 94.

In FIG. 5, tubing shapers 50a and 50b are shown moving in opposite directions, away from pumping portion 34b of the flexible tubing as plunger 48 descends to compress flexible tubing 34, displacing fluid from pumping portion 34b. To further enhance the repeatability and consistency of the volumetric capacity defined in pumping portion 34b of the flexible tubing, plunger cam track 152 is sized and shaped so that plunger 48 never completely compresses pumping portion 34b of the flexible tubing, even at the lower-most point of the plunger's reciprocal stroke. In addition, at the top of its reciprocal stroke, plunger 48 remains in contact with pumping portion 34b of the flexible tubing. The range of diametrical compression of flexible tubing 34 is from about 15% at the top of the pumping stroke to about 85% at the bottom of the pumping stroke of plunger 48. Since flexible tubing 34 need not recover to a fully uncompressed condition, i.e., to a perfect circular cross section, changes in the elasticity of flexible tubing 34 due to continued use and repeated compression have much less effect on the volumetric capacity of pumping portion 34b of the flexible tubing than would otherwise occur.

Torque Compensation

FIG. 6 illustrates details of torque compensation track 170, which is disposed on the back side of cam assembly 142. As shown in FIGS. 7A through 7C, torque compensation roller 172 rotates on a pin 173a set within a journal or bearing 173b. The ends of pin 173a are mounted in a head 173 that is attached to a distal end of flexure 174. The opposite end of flexure 174 is affixed to a mount 175, which includes clips 177 and 179 that are inserted into corresponding slots (not shown) within frame 100 (shown in FIG. 4) to hold the torque compensation in place. Flexure 174 biases the torque compensation roller 172 against the torque compensation track with sufficient force to provide the required compensating torque.

The profile or displacement of torque compensation track 170 from a plane varies about the axis of rotation of the cam assembly in a direction generally parallel to camshaft 144 (longitudinally in respect to the axis of rotation of the cam assembly). The extent of the displacement and its rate of change are defined at each point along the torque compensation track so as to compensate for the total net torque developed at a corresponding point on each of the other three cam tracks 140, 150, and 152 on cam assembly 142, as the corresponding cam followers travel along rapidly changing radial pitches of those tracks. A rapid radial change in the profile of one or more of these cam tracks develops a tangential force, producing an angular torque tending to rotate cam assembly 142. This torque can overdrive motor 146 beyond its desired speed, or load it, tending to slow the rotation of cam assembly 142. To compensate and prevent any variation in the speed of cam assembly 142, torque compensation track 170 is profiled to develop an opposing or off-setting torque that acts on cam assembly 142.

Torque compensation roller 172 has a conical tapered shape and is mounted on torque compensation flexure 174 at an angle "A" corresponding to the cone angle of the roller to accommodate the different rates of linear travel of torque compensation roller 172 along the radially inner and outer edge of torque compensation track 170. A round torque compensation roller would scrub and wear if used in place of conical or tapered shaped torque compensation roller 172, due to the radial force that would be developed between a round torque compensation roller and the surface of torque compensation track 170.

Figure 11:
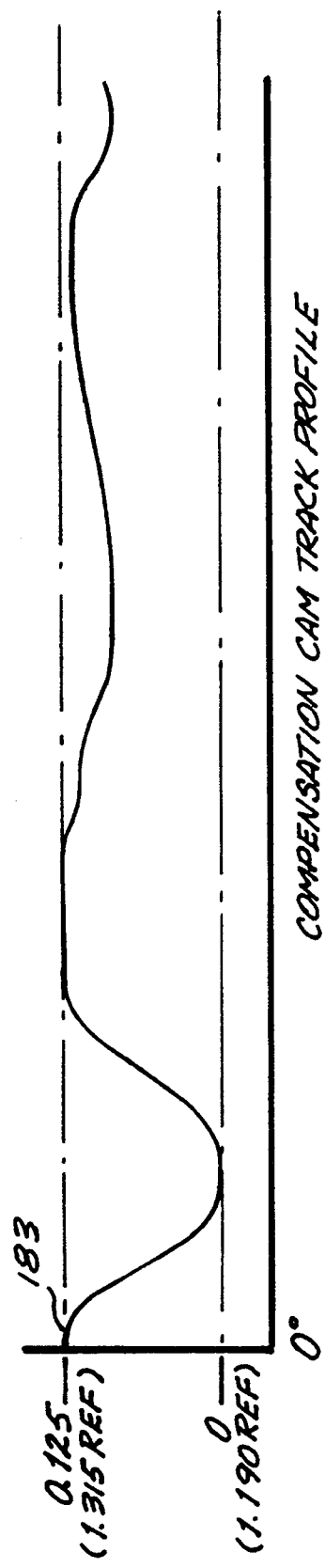
FIG. 11 is a graph showing the torque compensation track profile as a function of rotation angle of the cam assembly, referenced to a home position at 0 degrees for the cam tracks shown in FIGS. 8–10.

FIGS. 8, 9, and 10 illustrate the profile of inlet valve cam track 140, outlet valve cam track 150, and plunger cam track 152 in respect to the home position, which is indicated at the bottom of each of the cam track profiles at 0° rotation. Each pumping cycle of volumetric pump 30 corresponds to 360° of rotation of cam assembly 142 from the home position shown in FIGS. 8, 9, and 10. In FIG. 11, a compensation track profile 183 is graphically illustrated in respect to angular position or rotation of cam assembly 142. In this Figure, 0° of rotation corresponds to the home position of each cam track profile, as shown in FIGS. 8, 9, and 10.

Figure 12:
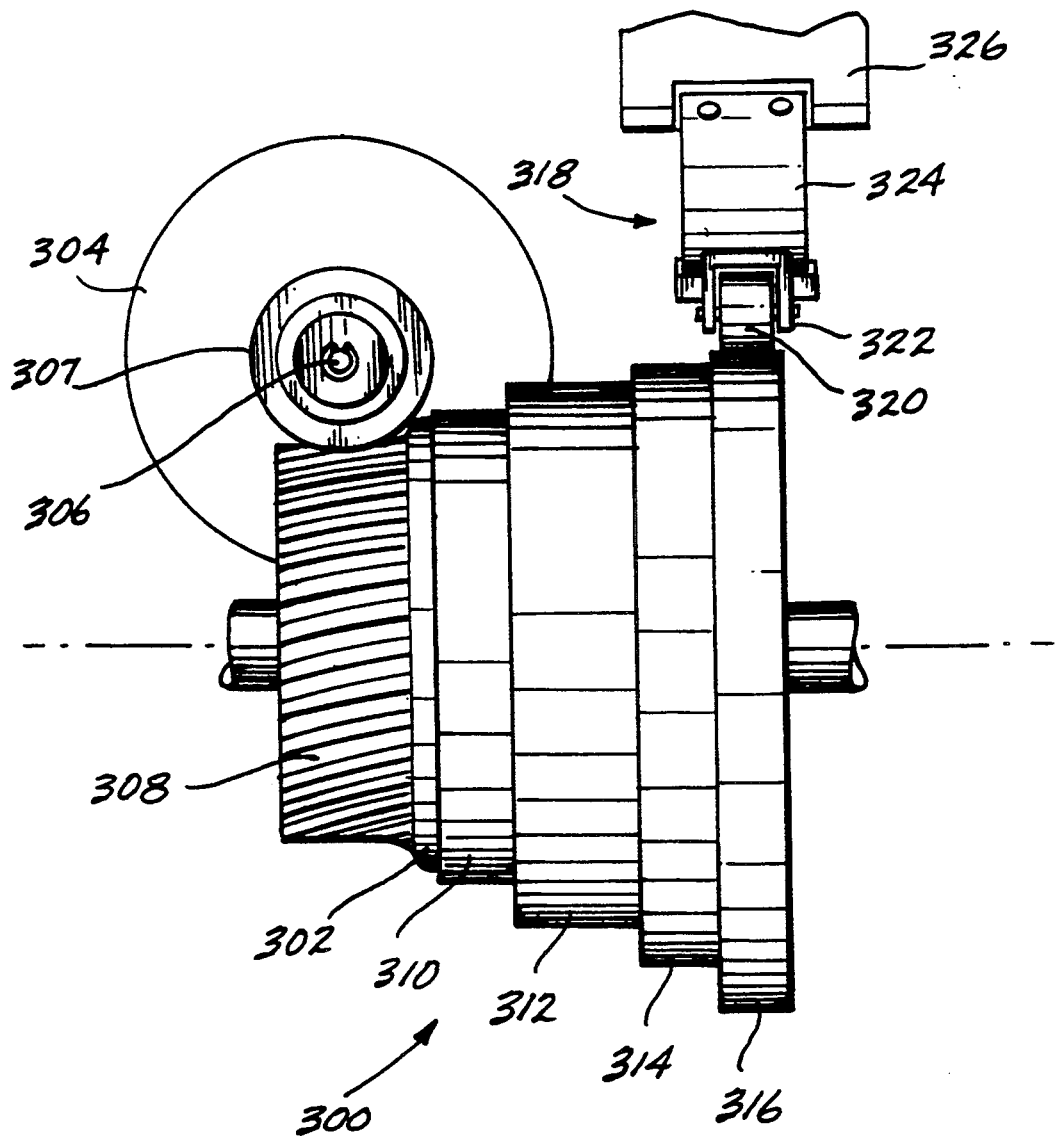
FIG. 12 is a plan view showing a cam assembly and torque compensation follower in accordance with a second embodiment of the present invention.

Referring now to FIG. 12, a second embodiment of a torque compensated cam assembly in accordance with the present invention is shown generally at reference numeral 300. Torque compensated cam assembly 300 includes a cam 302 that is rotatably driven by an electric motor 304. A drive shaft 306 rotates a helical gear 307 that drivingly engages splines 308 formed on one end of cam 302. Cam 302 includes a plurality of tracks 310, 312, and 314, each of which defines a profiled surface that actuates a different cam follower (not shown). These tracks 310, 312, and 314 produce a varying total net torque that at times tends to aid and at times tends to impede rotation of cam 302 by motor 304. To compensate the changing net torque during the rotation of cam 302, a torque compensation track 316 is provided circumferentially around cam 302, configured much like the other tracks, but with a profile selected to compensate the net total torque developed by the other tracks. Accordingly, a torque compensation follower 318 develops a compensating torque that substantially cancels the total net torque developed by the cam followers as they roll along tracks 310, 312, and 314. Torque compensation cam follower 318 includes a round roller 320 that is biased against torque compensation track 316 by a flat spring metal flexure 324. Flexure 324 is connected to a mount 326 at one end and roller 320 is rotatably mounted in a head 322 at its other end. The profile of torque compensation track thus produces a torque that is substantially equal in magnitude, but directed so as to tend to rotate cam 302 in the opposite direction, compared to the total net torque developed by the cam followers that roll along tracks 310, 312, and 314.

While the present invention has been disclosed in respect to its preferred embodiments and modifications thereto, those of ordinary skill in the art will understand that further modifications may be made within the scope of the claims that follow. Accordingly, it is not intended that the claims in any way be limited by the disclosure of these preferred embodiments, but that the scope of the invention be determined entirely by reference to the claims.

The invention in which an exclusive property or privilege is claimed is defined as follows:

1. A torque compensated cam assembly, comprising:
   a. a cam having an axis of rotation and a surface defining a path at a variable distance from the axis of rotation;
   b. a cam follower disposed in contact with said surface, the cam follower moving along said surface and experiencing a radially directed force due to its contact with said surface as the cam rotates, the contact between said surface and the cam follower also producing a varying tangential force that acts on the cam as the cam follower moves toward and away from the axis of rotation as the cam follower tracks along said surface of the cam, thus producing a varying torque acting on the cam;
   c. a torque compensation track disposed on the cam and having a non-planar surface configured in an inverse relationship to said surface of the cam;
   d. a torque compensation follower that is in moving contact with the non-planar surface of the torque compensation track as the cam rotates; and
   e. a spring connected to bias the torque compensation follower against the non-planar surface of the torque compensation track, producing a compensating torque that is substantially equal and opposite to the varying tangential torque produced by the cam follower.

2. The torque compensated cam assembly of claim 1, wherein the torque compensation track is disposed on an end of the cam and the non-planar surface moves the torque compensation follower back and forth longitudinally generally parallel with the rotational axis as the cam rotates.

3. The torque compensated cam assembly of claim 2, wherein the surface of the torque compensation track has a width that extends generally radially with respect to the rotational axis, and wherein the torque compensation follower comprises a roller that rolls along the surface of the torque compensation track, the roller being tapered to match the linear velocity of said surface at opposite points separated by the width of the torque compensation track, a radially inner side of said surface traveling at a substantially slower linear velocity than a radially outer side thereof as the cam turns about its rotational axis, the roller tapering from a larger diameter on a radially outer side thereof, toward a smaller diameter on a radially inward side, at an angle selected to compensate for the differences in linear velocity across the width of said surface of the torque compensation track.

4. The torque compensated cam assembly of claim 2, wherein the torque compensation follower comprises a roller, and wherein the spring comprises an elastic flexure fixedly mounted at one end, the roller being mounted on another end of the flexure so that it is biased thereby into rolling contact with the surface of the torque compensation track.

5. The torque compensated cam assembly of claim 1, wherein the cam follower comprises a spring-biased roller that rolls along the surface of the path, said path being defined generally circumferentially about the cam.

6. The torque compensated cam assembly of claim 1, wherein the torque compensation track is generally circumferentially disposed about the central rotational axis of the cam, so that its surface is at a variable radial distance from the rotational axis.

7. A torque compensated cam assembly, comprising:
   a. a cam having an axis of rotation and a plurality of surfaces, each defining a path at a variable distance from the axis of rotation;
   b. a plurality of cam followers, each disposed in contact with a different one of said surfaces, so that each cam follower is acted upon by a radially directed force due to its contact with said one surface as the cam rotates, the contact between said one surface and said cam follower also producing a varying tangential force that acts on the cam as said cam follower moves along said surface, a total of the tangential forces thus developed by all of the cam followers producing a varying total torque acting on the cam;
   c. a torque compensation track disposed on the cam and having a non-planar surface with a varying predefined shape;
   d. a torque compensation follower that is in contact with the non-planar surface of the torque compensation track as the cam rotates; and
   e. a spring connected to bias the torque compensation follower against the non-planar surface of the torque compensation track, producing a compensating torque that is substantially equal and opposite in the direction of rotation to the varying total torque produced by the plurality of cam followers, as the cam rotates about its axis of rotation.

8. The torque compensated cam assembly of claim 7, wherein the torque compensation track is disposed on an end of the cam, and wherein the non-planar surface moves the cam follower through a varying longitudinal displacement generally parallel with the axis of rotation of the cam.

9. The torque compensated cam assembly of claim 8, wherein the surface of the torque compensation track has a radial width that extends radially with respect to the axis of rotation and wherein the torque compensation follower comprises a roller that rolls along the surface of the torque compensation track, the roller being tapered to substantially match the linear velocity of said surface at points spaced apart across the width of the torque compensation track, a radially inner point on said surface traveling at a substantially slower linear velocity than a radially outer point thereon as the cam turns about its axis of rotation, the roller tapering from a larger diameter on a radially outer side, toward a smaller diameter on a radially inward side, at an angle selected to compensate for the differences in linear velocity across the width of said surface of the torque compensation track.

10. The torque compensated cam assembly of claim 8, wherein the torque compensation follower comprises a roller, and wherein the spring comprises an elastic flexure fixedly mounted at one end, the roller being mounted on another end of the flexure so that it is biased thereby into rolling contact with the surface of the torque compensation track.

11. The torque compensated cam assembly of claim 7, wherein the cam follower comprises a spring-biased roller that rolls along the surface of the path, said path being defined generally circumferentially about the cam.

12. The torque compensated cam assembly of claim 7, wherein the torque compensation track is generally circumferentially disposed about the axis of rotation of the cam, so that its surface is at a variable radial distance from the axis of rotation.

13. A torque compensated cam assembly for use in a reciprocating pump to maintain a substantially constant load on a prime mover that drives the pump, comprising:
  a. a cam rotatably driven by a prime mover to rotate about an axis;
  b. cam follower means that contact the cam at a varying radial distance from the axis as the prime mover rotates the cam about said axis, producing a torque that varies with a rotational position of the cam, said torque at times being directed so as to aid rotation and at other times being directed so as to impede rotation of the cam by the prime mover; and
  c. torque compensation means for producing a compensating torque that is generally equal and opposite in rotational direction to the torque produced by the cam follower means so that a substantially constant load is presented to the prime mover as it rotatably drives the cam.

14. The torque compensated cam assembly of claim 13, wherein the cam follower means comprise a plurality of cam followers that each follow s different path disposed circumferentially about the cam as the prime mover drivingly rotates the cam, each path comprising a surface that is at a varying radial distance about the axis of the cam.

15. The torque compensated cam assembly of claim 13, wherein the torque compensation means comprise a spring-biased roller that rolls along a track disposed on the cam, the track having a predefined profile to provide the compensating torque.

16. The torque compensated cam assembly of claim 15, wherein the track is disposed on one end of the cam, around the axis of the cam, and is generally circular, the predefined profile of the track varying in a direction generally parallel to the axis of the cam.

17. The torque compensated cam assembly of claim 15, wherein the roller is tapered at a predefined angle between a larger diameter side and a smaller diameter side, the predefined angle compensating for differences in a linear velocity of radially different points on the track.

18. The torque compensated cam assembly of claim 15, wherein the roller is mounted on a flexure that provides a spring-biasing force to produce the compensating torque.

19. The torque compensated cam assembly of claim 13, wherein the torque compensation means comprise a spring-biased roller that rolls along a track formed circumferentially about the cam and having a predefined profile selected to provide the compensating torque.

20. The torque compensated cam assembly of claim 13, wherein the cam follower means comprise a spring-biased roller that rolls circumferentially around the cam along a path that is disposed at a varying radial displacement from the axis of the cam, as a function of its angular position about said axis.

* * * * *